United States Patent [19]

Thiele et al.

[11] 4,224,307

[45] * Sep. 23, 1980

[54] MOUTHWASH AND METHODS

[75] Inventors: Geraldine H. Thiele, New Oxford, Pa.; Samuel L. Yankell, Moorestown, N.J.

[73] Assignee: Oxford Hill, Ltd., New Oxford, Pa.

[ * ] Notice: The portion of the term of this patent subsequent to Jun. 27, 1995, has been disclaimed.

[21] Appl. No.: 918,792

[22] Filed: Jun. 26, 1978

Related U.S. Application Data

[63] Continuation of Ser. No. 755,400, Dec. 29, 1976, Pat. No. 4,097,604 and a continuation-in-part of Ser. No. 890,239, Mar. 27, 1978 and a continuation of Ser. No. 642,114, Dec. 18, 1975, abandoned, and a continuation-in-part of Ser. No. 724,942, Sep. 20, 1976, abandoned and a continuation-in-part of Ser. No. 724,943, Sep. 20, 1976, abandoned and a continuation-in-part of Ser. No. 113,362, Feb. 8, 1971, Pat. No. 3,741,204, and a continuation-in-part of Ser. No. 123,830, Mar. 12, 1971, Pat. No. 3,767,812, and a continuation-in-part of Ser. No. 283,662, Aug. 25, 1972, Pat. No. 3,805,776, and a continuation-in-part of Ser. No. 283,663, Aug. 25, 1972, Pat. No. 3,828,772, and a continuation-in-part of Ser. No. 369,236, Jun. 12, 1973, Pat. No. 3,924,000, and a continuation-in-part of Ser. No. 483,010, Jun. 25, 1974, Pat. No. 3,982,017; said Ser. No. 890,239, is a continuation-in-part of Ser. Nos. 724,943 and 483,010 and a continuation-in-part of Ser. Nos. 369,236, 283,663, 283,662, 123,830, and 113,362; said Ser. No. 755,400, is a continuation of Ser. No. 642,114, and a continuation-in-part of Ser. Nos. 483,010, 369,236, 283,663, 283,662, 123,830, and 113,362; said Ser. No. 724,943, is a continuation of Ser. No. 483,010, and a continuation-in-part of Ser. Nos. 369,236, 283,663, 283,662, 123,830, and 113,362; said Ser. No. 724,942, is a continuation-in-part of Ser. Nos. 483,010, 369,236, 283,663, 283,662, 123,830, and 113,362; said Ser. No. 642,112, is a continuation-in-part of Ser. Nos. 483,010, 369,236, 283,663, 283,662, 123,830, and 113,362; said Ser. No. 483,010, is a continuation-in-part of Ser. Nos. 369,236, 283,663, 283,662, 123,830, and 113,362; said Ser. No. 369,236 is a continuation-in-part of Ser. Nos. 283,663, 283,662, 123,830, and 113,362; said Ser. No. 283,663, is a continuation-in-part of Ser. Nos. 283,662, 123,830 and 113,362; said Ser. No. 283,662 is a continuation-in-part of Ser. Nos. 123,830 and 113,362; said Ser. No. 123,830 is a continuation-in-part of Ser. No. 113,362.

[51] Int. Cl.$^2$ .................. A61K 7/36; A61K 31/20
[52] U.S. Cl. .................. 424/49; 424/57; 424/318
[58] Field of Search .................. 424/49, 57, 318

[56] References Cited

OTHER PUBLICATIONS

Hirsch—Chem. Abst. Vol. 41 (1947) pg. 5919e.
Teruzo et al—Chem. Abst. Vol. 48 (1954) pg. 11540i.
Prinz—Dental Formulary (1923) pp. 144–145.

*Primary Examiner*—Delbert R. Phillips
*Assistant Examiner*—Blondel Hazel
*Attorney, Agent, or Firm*—Fisher, Christen & Sabal

[57] ABSTRACT

The mouthwash is a liquefied composition of an effective amount of a non-necrotic fatty acid compound prepared from an unsubstituted, unsaturated fatty acid having at least one double bond, water, an effective amount of a buffering agent, 1 to 10 percent of ethanol, and at least one oil soluble flavorant. The pH of the liquefied composition is between 9 and 11.

9 Claims, No Drawings

MOUTHWASH AND METHODS

This application is a continuation of application Ser. No. 755,400, which was filed on Dec. 29, 1976, now U.S. Pat. No. 4,097,604, is a continuation-in-part of application Ser. No. 890,239, which was filed on Mar. 27, 1978, is a continuation of application Ser. No. 642,114, which was filed on Dec. 18, 1975, now abandoned, is a continuation-in-part of application Ser. No. 724,942, now abandoned, which was filed on Sept. 20, 1976, is a continuation-in-part of application Ser. No. 724,943, which was filed on Sept. 20, 1976, now abandoned, is a continuation-in-part of application Ser. No. 113,362, which was filed on Feb. 8, 1971, now U.S. Pat. No. 3,741,204, is a continuation-in-part of application Ser. No. 123,830, which was filed on Mar. 12, 1971, now U.S. Pat. No. 3,767,812, is a continuation-in-part of application Ser. No. 283,662, which was filed on Aug. 25, 1972, now U.S. Pat. No. 3,805,776, is a continuation-in-part of application Ser. No. 283,663, which was filed on Aug. 25, 1972, now U.S. Pat. No. 3,828,772, is a continuation-in-part of application Ser. No. 369,236, which was filed on June 12, 1973, now U.S. Pat. No. 3,924,000, and is a continuation-in-part of application Ser. No. 483,010, which was filed on June 25, 1974, now U.S. Pat. No. 3,982,017; application Ser. No. 890,239 is a continuation of application Ser. No. 724,943, is a continuation of application Ser. No. 483,010, is a continuation-in-part of application Ser. No. 369,236, is a continuation-in-part of application Ser. No. 283,663, is a continuation-in-part of application Ser. No. 283,662, is a continuation-in-part of application Ser. No. 123,830, and is a continuation-in-part of application Ser. No. 113,362; application Ser. No. 755,400 is a continuation of application Ser. No. 642,114, is a continuation-in-part of application Ser. No. 483,010, is a continuation-in-part of application Ser. No. 369,236, is a continuation-in-part of application Ser. No. 283,663, is a continuation-in-part of application Ser. No. 283,662, is a continuation-in-part of application Ser. No. 123,830, and is a continuation-in-part of application Ser. No. 113,362; application Ser. No. 724,943 is a continuation of application Ser. No. 483,010, is a continuation-in-part of application Ser. No. 369,236, is a continuation-in-part of application Ser. No. 283,663, is a continuation-in-part of application Ser. No. 283,662, is a continuation-in-part of application Ser. No. 123,830 and is a continuation-in-part of application Ser. No. 113,362; application Ser. No. 724,942 is a continuation-in-part of application Ser. No. 483,010, is a continuation-in-part of application Ser. No. 369,236, is a continuation-in-part of application Ser. No. 283,663, is a continuation-in-part of application Ser. No. 282,662, is a continuation-in-part of application Ser. No. 123,830, and is a continuation-in-part of application Ser. No. 113,362; application Ser. No. 642,112 is a continuation-in-part of application Ser. No. 483,010, is a continuation-in-part of application Ser. No. 369,236, is a continuation-in-part of application Ser. No. 283,663, is a continuation-in-part of application Ser. No. 283,662, is a continuation-in-part of application Ser. No. 123,830, and is a continuation-in-part of application Ser. No. 113,362; application Ser. No. 483,010 is a continuation-in-part of application Ser. No. 369,236, is a continuation-in-part of application Ser. No. 283,663, is a continuation-in-part of application Ser. No. 283,662, is a continuation-in-part of application Ser. No. 123,830, and is a continuation-in-part of application Ser. No. 113,362; application Ser. No. 369,236 is a continuation-in-part of application Ser. No. 283,663, is a continuation-in-part of application Ser. No. 283,662, is a continuation-in-part application of Ser. No. 123,830 and is a continuation-in-part of application Ser. No. 113,362; application Ser. No. 283,663 is a continuation-in-part of application Ser. No. 123,830 and is a continuation-in-part of application Ser. No. 113,362; application Ser. No. 283,662 is a continuation-in-part of application Ser. No. 123,830 and is a continuation-in-part of application Ser. No. 113,362; and application Ser. No. 123,830 is a continuation-in-part of application Ser. No. 113,362.

FIELD OF THIS INVENTION

This invention relates to a mouthwash.

BROAD DESCRIPTION OF THIS INVENTION

An object of this invention is to provide a mouthwash for the prevention of dental caries, prevention and removal of dental plaque and calculus, the treatment and prevention of gingivitis and related peridontal diseases, the alleviation, reduction, elimination and prevention of the sensitive teeth syndrome, and the like. Other objects and advantages of this invention are set out elsewhere herein or are obvious to one ordinarily skilled in the art herefrom.

This invention achieves the objects the advantages of this invention.

This invention involves a mouthwash. The mouthwash is a liquefied composition of an effective amount of a non-necrotic fatty acid compound prepared from an unsubstituted, unsaturated fatty acid having at least one double bond, water, an effective amount of a buffering agent, 1 to 10 percent of ethanol, and an effective amount of at least one oil soluble flavorant. The pH of said liquefied composition being between 9 and 11. Sweetners can be incorporated in the mouthwash. The mouthwash can be usd as a dentifrice by adding an effective amount of a thickener.

Oil soluble flavorants have a serious problem with pH drift, i.e., the pH greatly drops in a very short period of time, when the ethanol content of the mouthwash is above 10 percent. Water soluble flavorants do not have the same problem, but they do not have as good flavoring properties. The pH of this invention is critical and most preferably should be between 9.6 and 10 (best at 9.8). At above 10 percent, the ethanol ionizes or reacts in the hydro alcoholic solution. The use of a buffer is also critical to prevent pH drift. (The pH, for example, can be adjusted to about 10.5 and then lowered to 9.8 with a buffer such as disodium phosphate or sodium phosphate, or a buffer such as disodium phosphate or sodium phosphate can be added and then the pH adjusted to 9.8 with NaOH.) The flavorant methyl salicylate (even 0.1 and 0.2 percent) causes severe pH drift even at a 5 percent ethanol level with buffering. Any flavorant containing an ester linkage may cause an unstable pH at the high ethanol levels due to reaction with the ester linkage. So the ethanol content should be 1 to 10 percent, preferably 3 to 7.5 percent, and most preferably 5 percent, when an oil soluble flavorant(s) is used.

This invention includes the method of treating teeth for the prevention of caries or tooth decay by contacting the teeth with a sufficient and effective amount of the mouthwash to achieve the purpose. The plaque-forming bacteria are removed and kept from proliferating so that more plaque cannot be formed on the teeth. This invention also includes a method of treating teeth for the removal of dental plaque and/or dental calculus from teeth and the prevention of the formulation of dental plaque and/or dental calculus on teeth by contacting the teeth with a sufficient and effective amount of the mouthwash to achieve such purpose and then removing the plaque by means of light brushing or the like. The removal, etc., of the plaque-forming bacteria results in the stoppage of plaque formation and its weakening and losening so it can easily be removed.

This invention includes a method of treating and preventing gingivitis anf related peridontal diseases by contacting the effected and diseased gums (gingival tissue) with a sufficient and effective amount of the mouthwash to achieve the purpose. This embodiment is useful in preventing and treating of certain periodontal diseases, for example, inflammations of the gums such as, gingivitis and parulis, gingival retraction, receeding of the gum, such as, ulatrophy, etc. Gingivitis is inflammation of the gingival tissues. Types of gingivitis are functional gingivitis, gingivitis marginal and cotton-roll gingivitis. By the treating and alleviating and curing periodontal diseases, such as, gingivitis, with the mouthwash of this invention, lose teeth are tightened with a return to healthy gums. The healthier gums, which have often receded down and away from teeth, frequently return to and near their original positions.

DETAILED DESCRIPTION OF THIS INVENTION

The composition of this invention should not be stored in plastic bottles as plastics often deactivate the double bond of the unsaturated fatty acid salt in the composition of this invention. The result is a lowering of the effectiveness of the composition of this invention.

The mouthwash of this invention: is easily applied; is rapid in action; can be used for prolonged period of time; does not irritate the pulp; is painless; is consistently effective; and does not stain the teeth.

The flavorant can be a flavoring oil, such as, oil of peppermint, oil of spearmint, oil of colve, oil of lemon, oil of almond, oil of nutmeg, oil of orange, oil of wintergreen, oil of anise, oil of nutmeg, oil of savory, oil of cinnamon, oil of celery, oil of rosemary and oil of thyme (the above are ethanol falvoring extracts). Other flavorants include vanilla, lime, banana, cherry, brandy, rum, butterscotch, imitation brandy and synthetic vanilla. Artificial and natural flavorants can be used. Sweetners, such as, sorbitol, can be used. Any suitable colorant (e.g., FD & C Blue No. 1) can be used.

The teeth should be brushed regularly to help assure clean teeth for the mouthwash to be most effective upon. The teeth do not have to be mechanically scraped, or the like, because the mouthwash of this invention is effective against plaque-forming bacteria (and subsequently the plaque itself comes off with the aid of light brushing).

The composition of this invention is an effective antimicrobial agent.

A dentifrice can be used in place of the mouthwash by the addition of a thickener to the dentifrice. The thickener can be any suitable carrier or base material which forms a paste or the like. Useful thickeners are: methylcellulose; modified starches (5 to 40 percent by weight based on the total gel weight); polyvinyl alcohol (up to 7 percent by weight based on the total gel weight); gelatin (5 to 30 percent by weight based on the total gel weight); Carbowax; hydroxymethyl cellulsoe or hydroxyethyl cellulose or hydroxypropyl cellulose or methyl cellulose (2 to 20 percent by weight based on the total gel weight); glycerin (preferred); metallic salts of fatty acids (15 percent and above produces a gel); fatty acid esters (e.g., propylene glycol ethers of oleic acids); a water-miscible base made from propylene glycol, stearic acid, diglycol stearate and triethanolamine; glycerin and polyethylene glycol; water-dispersible petroleum base containing octylphenoxyethanol; polyethylene glycol; water miscible base compound of propylene glycol monostearate, isopropyl myristate, propylene glycol, stearic acid, sorbitol, water and polyoxyethylene sorbitan monopalmitate; polyethylene glycols and propylene glycol cetyl alcohol, stearyl alcohol, spermacetic; polyoxyl 40 stearate; polyoxyl 8 stearate, water and glycerine; glycerin, cetyl alcohol, mineral oil, an ethoxylated fatty alcohol, water, methylparaben and polylparaben. Useful thickeners which form thixotropic gels can be: sodium carboxymethylcellulose (0.5 to 25 percent by weight based on the total gel weight); and polyvinyl propylene (Pasdone C, made by GAF) (1 to 30 percent by weight based on the total gel weight). To form thixotropic gels, which art knows that certain concentrates of the gel base having a particular viscosity property or molecular weight need be used.

In general, the thickener, should be non-drying and water-miscible or water-soluble. The thickner can be an emulsifier. THe thickner should be odorless, non-irritating and non-toxic. The thickner can be colorless or colored.

One advantage of the use of a thickner is that such helps minimizes the stability problems by suspending the chemical action. THe thickner increases the shelf life of, for example, sodium oleate by slowing down the hydrolysis thereof.

Usage can be, for example, by placing a few drops of the dentifrice on a toothbrush—care should be used to insure brushing of the gum lines.

The most preferred mouthwash composition of this invention is a liquefied composition comprising a sterile aqueous solution containing 5 percent of sodium oleate, 5 percent of ethanol, 10 percent of sorbitol, 0.3 percent of disodium phosphate, 0.1 percent menthol, 0.15 percent of oil of peppermint, and 0.05 percent of oil of clove, and which has a pH of 9.8.

The term liquefied composition includes slurries, suspensions, solutions dentifrices, etc.

All of the components of the liquefied composition must be and are substantially non-toxic in the amounts and under the conditions of use. The useful (sclerosing) fatty acid compounds must be non-necrotic in effect or operation and must not cause the pathologic death of one or more cells, or a portion of any tissue or any organ, resulting from irreversible damage to the nucleus.

The pH of the liquefied composition should be between about 9 and about 11, and preferably between about 9 and about 10. Each non-necrotic (sclerosing) unsaturated fatty acid compound will produce a different pH at a different concentration levels, so non-toxic agents may be added to adjust the pH level, e.g., sodium dihydrogen phosphate or sodium hydroxide can be used when sodium oleate or another non-necrotic (sclerosing) unsaturated fatty acid compound is used.

It should be noted that aqueous solutions of alkali metal salts of fatty acids in general have an alkaline or neutral pH. For example, sodium oleate has an alkaline pH—this is usually due to hydrolysis in the aqueous solution.

The most preferred unsaturated fatty acids have eighteen carbon atoms with one double bond in the middle of the chain. The most preferred of such fatty acids is oleic acid (i.e., cis-9-oleic acid or cis-9-octadecenoic acid). The next preferred of such fatty acids is elaidic acid (i.e., trans-9-octadecenoic acid).

Examples of other unsaturated fatty acids having one double bond (i.e., monoethenoid fatty acids) having eighteen carbon atoms are: 2-octadecenoic acid (cis and trans forms), $CH_3(CH_2)_{14}CH=CHCOOH$; 3-octadecenoic acid, $CH_3(CH_2)_{13}CH=CHCH_2COOH$; 4-octadecenoic acid, $CH_3(CH_2)_{12}CH=CH(CH_2)_2COOH$; 5-octadecenoic acid, $CH_3(CH_2)_{11}CH=CH(CH_2)_3COOH$; 6-octadecenoic acid (cis and trans forms), $CH_3(CH_2)_{10}CH=CH(CH_2)_4COOH$; 7-octadecenoic acid (cis and trans forms), $CH_3(CH_2)_9CH=CH(CH_2)_5COOH$; 8-octadecenoic acid (cis and trans forms; 10-octadecenoic acid, (cis and trans form), $CH_3(CH_2)_6CH=CH(CH_2)_8COOH$; 11-octadecenoic acid (cis and trans form), $CH_3(CH_2)_5CH=CH(CH_2)_9COOH$; 12-octadecenoic acid (cis and trans form), $CH_3(CH_2)_4CH=CH(CH_2)_{10}COOH$; 15-octadecenoic acid (trans form), $CH_3CH_2CH=CH(CH_2)_{13}COOH$; 16-octadecenoic acid (trans form), $CH_3CH=CH(CH_2)_{13}CH_2COOH$; and 17-octadecenoic acid $CH_2=CH(CH_2)_{14}CH_2COOH$ (It is believed that the fatty acids having the unsaturation at one end of the hydrocarbon chain, or not in the center thereof, have some undesirable properties and effects in the processes of this invention, e.g., less complete and slower dental plaque removal and prevention—such compounds are useful, but are certainly must less preferred in result.)

Examples of other useful monoethenoid fatty acids are: 2-tridecenoic acid; 11-tridecenoic acid; 12-tridecenoic acid; 2-dodecenoic acid; 5-dodecenoic acid; 6-dodecenoic acid; 7-dodecenoic acid; 9-dodecenoic acid; 10-dodecenoic acid; 11-dodecenoic acid; 9-eicosenoic acid, $CH_3(CH_2)_9CH=CH(CH_2)_7COOH$; 11-eicosenoic acid; 14-eicosenoic acid; 2-undecenoic acid; 6-undecenoic acid; 9-undecenoic acid; 10-undecenoic acid; 2-decenoic acid; 3-decenoic acid; 4-decenoic acid; 8-decenoic acid; 9-decenoic acid; acrylic acid, $CH_2=CHCOOH$; β-methylacrylic acid(cis and trans forms), $CH_3CH=CHCOOH$; α-methylacrylic acid, $CH_2=C(CH_3)COOH$; vinyl acetic acid, $CH_2=CHCH_2COOH$; β,β-dimethylacrylic acid, $(CH_3)_2C=CHCOOH$; β-pentenoic acid, $CH_3CH=CHCH_2COOH$; allylacetic acid, $CH_2=CHCH_2CH_2COOH$; angelic acid, $CH_3CH=C(CH_3)COOH$ (cis form); tiglic acid, $CH_3CH=C(CH_3)COOH$ (trans form); 2-heptadecenoic acid, $CH_3(CH_2)_{12}CH_2CH=CHCOOH$; 9-heptadecenoic acid (cis and trans forms), $CH_3(CH_2)_6CH=CH(CH_2)_7COOH$; 2-hexadecenoic acid, $CH_3(CH_2)_{12}CH=CHCOOH$; 9-hexadecenoic acid (cis form); 2-tetradecenoic acid; 4-tetradecenoic acid; 5-tetradecenoic acid; 8-tetradecenoic acid; 9-tetradecenoic acid; 2-nonenoic acid; 3-nonenoic acid; 8-nonenoic acid; 2-octenoic acid; 3-octenoic acid; 7-octenoic acid; 2-heptenoic acid; 3-heptenoic acid; 4-heptenoic acid; 5-heptenoic acid; 6-heptenoic acid; 2-hexenoic acid; 3-hexenoic acid; 4-hexenoic acid; 5-hexenoic acid; 15-tetracosenoic acid; 17-hexacosenic acid; and 21-triacentenoic acid.

Examples of fatty acids having a triple bond are: 2-nonynoic acid, $CH_3(CH_2)_5C\equiv CCOOH$; 3-nonynoic acid; 4-nonynoic acid; 5-nonynoic acid; 6-nonynoic acid; 7-nonynoic acid; and 8-nonynoic acid.

Examples of diethenoid fatty acids having eighteen carbon atoms are: 6:8-octadecadienoic acid, $CH_3(CH_2)_8CH=CHCH=CH(CH_2)_4COOH$; 8:10-octadecadienoic acid, (8-trans and 10-trans forms); 8:11-octadecadienoic acid, (8-cis and 11-cis forms); 9:11-octadecadienoic acid, (9-cis and 11-cis and 11-trans forms); 5:12-octadecadienoic acid, (5-cis, 5-trans, 12-trans and 12-cis forms); 9:12-octadecadienoic acid, (9-cis, 9-trans, 12-trans and 12-cis forms); 10:12-octadecadienoic acid, (10-cis, 10-trans, 12-cis and 12-trans forms); 10:13-octadecadienoic acid, (10-cis and 13-cis forms); and 11:14-octadecadienoic acid, (11-cis and 14-cis forms).

Examples of other useful diethenoid acids are β-vinylacrylic acid, $CH_2=CHCH=CHCOOH$; sorbic acid, $CH_3CH=CHCH=CHCOOH$; and geranic acid; $(CH_3)_2C=CH(CH_2)_2C(CH_3)=CHCOCH$.

Examples of tetra-triethenoid fatty acid having eighteen carbon atoms are: 9:11:13:15-octadecatetraenoic acid, $CH_3CH_2(CH_2=CH_2)_4(CH_2)_7COOH$; 6:9:12:15-octadecatetraenoic acid; 5:9:12-octadecatrienoic acid (5-trans, 9-cis and 12-cis forms); $CH_3(CH_2)_4CH=CHCH_2CH=CH(CH_2)_2CH=CH(CH_2)_3COOH$; 6:9:12-octadecatrienoic acid; 6:10:14-octadecatrienoic acid; 8:10:12-octadecatrienoic acid (8-cis, 10-trans and 12 cis forms); 9:11:13-octadecatrienoic acid (9-cis, 11-trans and 13 trans forms); 9:12:15-octadecatrienoic acid (9-cis, 9-trans, 12-cis, 12-trans, 15-cis and 15-trans forms; and 10:12:14-octadecatrienoic acid (10-trans, 12-trans and 14-trans forms).

An example of a useful triethenoid fatty acid is dehydrogeranic acid, $(CH_3)_2C=CHCH=CHC(CH_3)=CHCOOH$.

Examples of fatty acids having four double bonds are clupandoic acid, moroctic acid, arachidonic acid, α-parinaric acid, and β-parinaric acid.

The useful unsaturated fatty acids can contains between 1 and 50 carbon atoms, preferably between 14 and 22 carbon atoms and most preferably by a wide margin have 18 carbon atoms.

Examples of useful unsaturated fatty acids are oleic acid, licanic acid, eleostearic acid and clupanodonic acid. The useful unsaturated fatty acids can be those containing one double bond, e.g., oleic acid, two double bonds, e.g., linoleic acid, three double bonds, e.g., eleostearic acid, etc.

Within the scope of this invention, saturated fatty acid compounds are not useful. The mechanism requires fatty acid moiety unsaturation. Compositions containing mixtures of saturated and unsaturated fatty acid compounds, e.g., sodium morrhuate, should not be used due to the presence of any substantial amount of saturated fatty acid compounds. Sodium morrhuate is a mixture of the sodium salts of unsaturated and saturated fatty acids of cod liver oil.

Fatty acids which contain one or more hydroxyl groups (not containing the acid portion), e.g., dihydroxystearic acid and ricinoleic acid, are not useful within the scope of this invention. For example, the negative hydroxyl group in ricinoleic acid does not produce the necessary (cell) differentiation—this applies to all negative substituents on the main carbon chain. A high ammonia content will erode and "eat" the tooth enamel. These factors, plus degree of effectiveness, etc., are why the fatty acid compound should not be a substituted one. The fatty acid must not by cyclic. The fatty acid is probably not branch chained. The fatty acid should be straight chained, with unsaturation at the center of the carbon chain.

The fatty acid compounds can be soaps such as the reaction product of fatty acids and organic basis—but such are not preferred compounds. The fatty acid compounds can be esterified fatty acids. The fatty acid compound are most preferably a fatty acid salt. The fatty acid salts can be those prepared from metals such as, aluminum and alkaline earth metals, e.g., calcium, but are preferably those prepared by alkali metals, e.g., sodium (preferred), lithium, potassium, caesium and rubidium. (Ionic fatty acid compounds of sodium, such as, sodium oleate, are preferred even though the potassium salts are usually more soluble. Also, when the sodium balance becomes a factor, the sodium salts are the most preferred.) The metals are used as hydroxides, carbonates, etc. The fatty acid salts can be prepared from non-metallic inorganic bases, but such is not a preferred category of compounds.

The most preferred compound is sodium oleate.

Examples of useful compounds of oleic acid are: the methyl ester of cis-9-octadecenoic acid; ethyl ester of cis-9-octadecenoic acid; propyl ester of cis-9-octadecenoic acid; isopropyl ester of cis-9-octadecenoic acid; butyl ester of cis-9-octadecenoic acid; isobutyl ester of cis-9-octadecenoic acid; tert.-butyl ester of cis-9-octadecenoic acid; 3-methylbutyl ester of cis-9-octadecenoic acid; 2-methyl-2-butyl ester of cis-9-octadecenoic acid; phenyl ester of cis-9-octadecenoic acid; m-tolyl ester of cis-9-octadecenoic acid; p-phenylphenacyl ester of cis-9-octadecenoic acid; and the amide ester of cis-9-octadecenoic acid.

Examples of useful compounds of elaidic acid are: the methyl ester of trans-9-octadecenoic acid; the ethyl ester of trans-9-octadecenoic acid; and the amide ester of trans-9-octadecenoic acid.

Examples of useful octadecenoic acid compounds are: the methyl ester of trans-2-octadecenoic acid; the ethyl ester of trans-2-octadecenoic acid; the amide ester of trans-2-octadecenoic acid; the methyl ester of trans-3-octadecenoic acid; the methyl ester of cis-6-octadecenoic acid; the p-bromophenacyl ester of cis-6-octadecenoic acid; the amide of cis-6-octadecenoic acid; the triglyceride of cis-6-octadecenoic acid; the ethyl ester of trans-10-octadecenoic acid; the amide ester of trans-10-octadecenoic acid; the p-bromophenacyl ester of cis-11-octadecenoic acid; the methyl ester of trans-11-octadecenoic acid; the ethyl ester of cis-12-octadecenoic acid; and the methyl ester of trans-16-octadecenoic acid.

Examples of other useful monoethenoid fatty acid compounds are: the lithium salt of 9-heptadecenoic acid; the amide of 2-heptadecenoic acid; the methyl ester of 9-heptadecenoic acid; the ethyl ester of 9-heptadecenoic acid; the ethyl ester of 2-hexadecenoic acid; the methyl ester of 9-hexa decenoic acid; the ethyl ester of 9-hexadecenoic acid, the ethyl ester of 2-tetradecenoic acid; the methyl ester of 4-tetradecenoic acid; the ethyl ester of 4-tetradecenoic acid; the methyl ester of 9-tetradecenoic acid; the amide ester of 2-tridecenoic acid; the methyl ester of 12-tridecenoic acid; the ethyl ester of 12-tridecenoic acid; the amide of 7-dodecenoic acid; the ethyl ester of 11-dodecenoic acid; the methyl ester of 11-dodecenoic acid; the amide of 9-eicosenoic acid; the ethyl ester of 9-eicosenoic acid; the methyl ester of 11-eicosenoic acid; the amide of 2-undecenoic acid; the amide of 6-undecenoic acid; the ethyl ester of 9-undecenoic acid; the copper salt of 10-undecenoic acid; the ethyl ester of 10-undecenoic acid; the amide of 10-undecenoic acid; the amide of 2-decenoic acid; the methyl ester of 8-decenoic acid; the ethyl ester of 2-nonenoic acid; the ethyl ester of 8-nonenoic acid; the ethyl ester of 7-octenoic acid; the methyl ester of 7-octenoic acid; the amide of 2-octenoic acid; the methyl ester of 4-heptenoic acid; the methyl ester of 2-hexenoic acid; the ethyl ester of 2-hexenoic acid; the amide of 3-hexenoic acid; the methyl ester of 5-hexenoic acid; the ethyl ester of 2-pentenoic acid; and the amide of 15-tetracosenoic acid.

Examples of useful diethenoid fatty acid compounds having eighteen carbon atoms are: the methyl ester of 6:8-octadecadienoic acid; the methyl ester of 9:11-octadecadienoic acid; the ethyl ester of 9:11-octadecadienoic acid; the sodium salt of 9:12-octadecadienoic acid; the methyl ester of 9:12-octadecadienoic acid; the ethyl ester of 9:12-octadecadienoic acid; the amide of 9:12-octadecadienoic acid; the benzyl amide of 9:12-octadecadienoic acid; and the methyl ester of 10:12-octadecadienoic acid.

Examples of useful triethenoid fatty acid compounds having eighteen carbon atoms are: the methyl ester of 6:10:14-octadecatrienoic acid; the methyl ester of 9:11:13-octadecatrienoic acid; the ethyl ester of 9:11:13-octadecatrienoic acid; the methyl ester of 9:12:15-octadecatrienoic acid; the ethyl ester of 9:12:15-octadecatrienoic acid; and the methyl ester of 10:12:14-octadecatrienoic acid.

Examples of useful triple bond fatty acid compounds are: the methyl ester of 2-nonynoic acid; the methyl ester of 4-nonynoic acid; the methyl ester of 5- nonynoic acid; the methyl ester of 6-nonynoic acid; the methyl ester of 7-nonynoic acid; the methyl ester of 8-nonynoic acid; the amide of 2-nonynoic acid; the amide of 3-nonynoic acid; the amide of 4-nonynoic acid; the amide of 5-nonynoic acid; the methyl ester of 6-nonynoic acid; the amide of 7-nonynoic acid; and the amide of 8-nonynoic acid.

The purity of the unsaturated fatty acid compound is important. A composition containing a high percentage of unsaturated fatty acid moieties will not be very effective and can cause tissue, etc., damage and other problems. The preferred sodium oleate is particularly effective, while quite innocuous in a toxic and necrotic sense.

The mouthwash would contain between about 0.5 and about 10 percent by weight of the fatty acid compound, and usually contains between about 1 and about 5 percent by weight the fatty acid compound.

Examples of the liquid carrier for the non-necrotic fatty acid compounds are water (preferred) monoglycerides, diglycerides, etc. A mixture of water and ethanol is the most preferred liquid carrier; a salt (NaCl) can be added to make an isotonic aqueous solution as the liquid carrier.

The mouthwash composition preferably contains a buttering agent, such as, sodium phosphate such as secondary sodium phosphate, sodium carbonate, or the salt of a weak organic acid with a strong base of which sodium citrate is an example. Examples of useful buffers are disodium hydrogen phosphate and sodium dihydrogen phosphate (preferred).

A buffer solution exerts control over large pH changes. The buffer capacity is directly proportional to the concentration of the buffer components. It is desirable to keep a high concentration of buffer components so that the pH does not shift during usage of the mouthwash. To achieve this, the sodium oleate (or the like) should be present in a relatively high concentration so that the buffer components are present in a relatively high concentration.

Ethanol is a solubilizing agent for the sodium oleate, but the ethanol appears to also have a promoting effect, or the like, on the sodium oleate activity. Other solubilizing agents could be used, but the total effectiveness would apparently not be anywhere near as great as when ethanol is used.

A preferred mouthwash composition is a liquefied composition comprising a sterile aqueous solution containing 1 to 10 percent of sodium oleate, 1 to 10 percent of ethanol, enough buffer to adjust the pH to 9 to 10, flavorant, sweetner and the remainder sterile distilled water. Preferably a phosphate buffer is used.

Another preferred mouthwash composition is a liquefied composition comprising a sterile aqueous solution containing 5 percent of sodium oleate, 5 percent of ethyl alcohol, enough sodium dihydrogen phosphate to adjust the pH to 9.8, flavorant(s), sweetner and the remainder sterile distilled water.

If desired, in preparing the most preferred composition the pH can be raised to about 10 by the use of sodium hydroxide before the sodium oleate is added. Then the pH is raised back up to 9.8 by the addition of sodium dihydrogen phosphate, for example.

A flavorant or flavorants, in small amounts, can be added. Lemon oil can be used a flavorant, but since it is acidic only small amounts should be used so as not to substantially disturb the crucial pH level. While oil of peppermint can be added as a flavorant can be used, do not use too much as it causes to much foam. Any foam-causing agent (outside of the crucial basic ingredients) should be avoided for they tend to keep the mouthwash away from the teeth surfaces. A coloring agent or agents, in small amounts, can be used. A pleasant-odor producing amounts, can be used. No such additives should be used which hinder the effectiveness of the composition of this invention.

Anodynes in amounts of up to and including about 5 percent by weight may be added. An anodyne is an agent which ahs the power to relieve pain. An example of a useful anodyne is benzyl alcohol.

Suitable preservations can be added in an amount not to exceed 0.5 percent by weight.

Up to about 5 weight percent, based on the weight of the total composition, of mild anesthetics and/or antiseptics can be added. Examples of such materials are chlorobutanol and benzyl alcohol.

In the preferred compositions using sodium oleate, the ethanol and phosphate buffer are pH level are believed to aid and complement the action of the sodium oleate in a slightly synergistic manner (and may provide the key to the extreme effectiveness of the most preferred composition).

The mouthwash of this invention is preferably used by rinsing or gargling with the mouthwash. Each rinsing or gargling should preferably be at least one minute in duration in order to assure treatment and prevention of the sensitive teeth syndrome, etc. One should rinse or gargle at least once a day with the mouthwash to assure treatment and prevention of the sensitive teeth syndrome, etc.

The mouthwash of this invention can also be placed (a few drops, for example) on a toothbrush and then used as a liquid dentifrice in order to treat and prevent the sensitive teeth syndrome, etc.

This invention includes any effective method of contacting the mouthwash with the teeth, mouth and/or gingivitis tissue.

The mouthwash can be applied as an aerosal spray using an inert aerosal propellant, e.g., mixture of trichloromonfluoromethane and dichlorodifluoromethane—this is not a very effective method of treating and preventing the sensitive teeth syndrome, but could be used. Application can be by means of a simple squeeze bottle (without any aerosal propellant). An important factor is the contacting of all of the teeth surfaces with the mouthwash and rinsing or gargling for a period of time assures such.

The mouthwash of this invention should not be used in a foam or effervescent form. (Sodium fluoride causes an excessive amount of fluoride.)

The mouthwash of this invention does not disrupt or destroy the normal mouth microflora, except for the plaque-forming bacteria, and does not upset the digestive system (no diarrhea, etc., occurs if the mouthwash is consumed).

Most unsaturated fatty acids are found as the less stable cis isomers rather than the more stable trans isomer. The trans isomers have a double bond that is not in a readily accessable position (the two carbon chain portions protrude in opposite directions), and do not give anywhere as good as results. For this reason, elaidic acid (the trans isomer of the cis isomer, oleic acid) does not give anywhere as good results as does oleic acid.

Fatty acids (cis form) that have two or more double bonds are too reactive to perform in the preferred manner. An example of such is linoleic acid which is too reactive, but is a cis form fatty acid, has two double bonds (somewhat centrally located) and has 18 carbon atoms.

Oleic acid which is $CH_3(CH_2)_7CH=CH(CH_2)_7COOH$, has a melting point of 13° C. Vaccenic acid, which is $CH_3(CH_2)_5CH=CH(CH_2)_9COOH$, has a melting point of 44° C. This illustrates another reason to have the double bond near the center of the carbon chain—generally such produces a lower melting point, which is important as a liquid fatty acid (salt) is then available over the normal range of usage of the mouthwash.

This invention involves mostly procedures and materials that can be self-administered by the user.

This invention involves a method of treating teeth for the treatment of, prevention of and elimination of the sensitive teeth syndrome. The process involves contacting the teeth with a sufficient and effective amount of a mouthwash to achieve such purpose. The mouthwash is a liquefied composition of an effective amount of a non-necrotic fatty acid compound prepared from an unsubstituted, unsaturated fatty acid having at least one double bond, a water carrier, an effective amount of a buffering agent and an effective amount of ethanol, the pH of said liquefied composition being between 9 and 11.

The most preferred mouthwash contains about 5 percent of sodium oleate, about 5 percent of ethanol, sweetner, flavorants, enough disodium hydrogen phosphate to adjust the pH to about 9.8, and the remainder water.

The mouthwash of mouthrinse can contain certain additives such as flavorants, colorants, and preservatives. The above type of additives should not be used if they cause stability problems. An example of a useful flavorant is articifical spearmint. Examples of useful preservatives are thymol and methyl parabenzene—preservatives are not preferred ingredients. An example of a preferred colorant is blue-green or aqua, but red colorants are not preferred because they would tend to hide any bleeding gums, etc.

The sensitive teeth syndrome has been shown to result from exposed dentine, which is the layer or portion of the teeth under the enamel layer. The dentin can become exposed by brushing the teeth in an improper manner, when gums recede for a number of reasons, by cracks in the enamel, by improper filling of cavities, etc. Dentine is very sensitive to heat or cold, particularly rapid temperature changes, increased pressure (say, from chewing), sweet agents, sour agents, even touch, etc. A large amount of pain is often associated with sensitive teeth.

Using sodium oleate (preferred) as illustrative, it is believed that the dentin and enamel take up the sodium oleate. The exact mechanism has not been determined, but the sodium oleate could cover the affected surface area, even possibly filling the pores and/or cracks. The sodium oleate may even bind the nerve endings. The treatment and elimination of the sensitive teeth syndrome may be permanent or long term in duration after treatment. Repeated and continued usage is recommended. Repeated daily usage appears to stop the pain associated with the sensitive teeth syndrome in about five days or hrs.

Another embodiment of this invention involves the method of treating and controlling gingivitis and related periodontal diseases of the gingival tissue.

This embodiment is useful in preventing and treating of certain periodontal diseases, for example, inflammations of the gums such as, gingivitis and parulis, gingival retraction, receeding of the gum, such as, ulatrophy, etc. Gingivitis is inflammation of the gingival tissues. Types of gingivitis are afunctional gingivitis, gingivitis marginal and cotton-roll gingivitis.

By the treating and alleviating and curing periodontal diseases, such as, gingivitis, with the mouthwash of this invention, lose teeth are tightened with a return to healthy gums. The healthier gums, which have often receded down and away from teeth, frequently return to and near their original positions.

Periodontitis, or pyorrhea, is a disease affecting the supporting tissues of the teeth including the gingiva, the membrane lining the sockets which the teeth lie, and the bones surrounding the teeth. The disease may initially be associated with conditions of constant irritation of the gingiva by dental calculus, food impaction, poor dental restorations, traumatic occlusion, or chemical irritants. So it is seen that this invention can prevent much of the periodontitis.

The gums may be seriously harmed by deposits of dental calculus (tartar), a combination of minerals and bacteria found in the mouth. The bacterial associated with tartar can secrete enzymes and endotoxins which can irritate the gums and cause an inflammatory gingivitis. As the gums become increasingly irritated by this process they have a tendency to bleed, lose their toughness and resiliency, and separate from the teeth, leaving periodontal pockets in which debris, secretions, more bacteria and toxins further accumulate. It is also possible for food to accumulate in these pockets, thereby providing nourishment for increased growth of bacteria and production of endotoxins and destructive enzymes. The pus that forms in this process is capable of destroying gum and bone tissue. A variety of bacteria are generally found to be present during the active stages of periodontal disease. Such organisms as streptocci, staphylococci, pneumococci, etc. are usually present, and are found in the purulent discharge as well as in the involved tissue, and may be absorbed into the general system through the lymphatics or venous blood stream.

The progression of the pyorrheic process usually begins with gingivitis, initiating at the margins of the gums, in which the gingiva become more tender and sensitive, and appear flabby, inflamed and swollen. Periodontal pockets become apparent, and infection takes place in these pockets. Because the periodontal pockets cannot be cleaned by brushing or the use of dental floss, infection becomes progressive and constant. Due to, among other things, the effect of the mouthwash of this invention has on the microorganism causing the invention, etc., in these advanced disease stages the mouthwash can cure and alleviate such advanced periodontal diseases.

A discussion of the theory of plaque formation, etc., is helpful as a background for this invention.

The initiation of the caries process is believed to be produced by the interplay of bacteria and a carbohydrate substrate in contact with a susceptible tooth surface. This interaction takes place within the dental plaque which is adherent to the tooth surface.

The first step is the deposition of a soft plaque on the tooth surface. Most of the plaque consists of dead and living bacterial surrounded by a gel-like organic matrix derived from the bacteria and saliva. Inorganic components from saliva and bacteria are also present within the plaque. It has been shown recently that the bacteria in the plaque utilizes sucrose to form extra-cellular dextran and levan which, together with salivary mucoprotein forms a "biological flue" that cements the bacteria and other particulate matter to the tooth surface.

The plaque appears as a whitish, glistening or dull mat on tooth surfaces. It is not soluble in water and acts as an effective diffusion barrier between the salivary buffers and the tooth surface. After ingesting sucrose, the pH of the plaque drops to about 5 and is maintained at that level for some time. This low pH probably produces the initial decalcification of the tooth surface in the process of caries development.

In the second phase, the plaque undergoes gradual calcification to form dental calculus. It is not known what initiates this calcification process. Bacteria must play a role in some way since conventional animals form much more calculus than their germ-free counterparts. When calcification of plaque occurs, it begins within and between the bacteria. Many foci of calcification begins within the plaque and with time, these foci coalesce.

Dental plaque or bacterial plaque is a mass of filamentous microorganisms and large variety of smaller froms to the surface of a tooth; depending on bacterial activity and environmental factors, can give rise to caries, calculus, or inflammatory chancres in adjacent tissue. *Stedman's Medical Dictionary*, 20th Ed., (1961), p. 1174. Phage is an agent causing destruction or lysis of microorganisms (e.g., bacteria). Plaque is an area cleared by a phage in a bacterial growth; tache vierge. Kenneth, J. H., "A Dictionary of Biological Terms", 8th Ed., D. Van Nostrand Co., Inc., (1963). Dental calculus is (i) tartar or (ii) calcified deposits formed around the teeth.

Stedman's, ibid., p. 249. Tartar is a brownish or yellow-brown deposit on the teeth, chiefly hydroxyapatite is an organic matrix. Stedman's. ibid., pp. 1483-84.

Dental caries is a localized, progressively destructive disease of the teeth that starts at the external surface (usually the enamel), with the apparent dissolution of the inorganic components by organic acids. These acids are produced in immediate proximity to the tooth by the enzymatic action of masses of microorganisms (in the bacterial plaque) on carbohydrates. The initial demineralization is followed by an enzymatic destruction of the protein matrix. Cavitation and direct bacterial invasion follow. In the dentin, demineralization of the walls of the tubules is followed by bacterial invasion and destruction of the organic matrix. Untreated dental carie progresses to the pulp, resulting in infection and its sequelae. Stedman's ibid., p. 268.

Applicant believes that the lactrobacilli makes the sugar in food gram negative, so that the sugar can then affix to the ridges of the teeth. The bacteria are attached to the ridges of the teeth. The plaque formed is a gram negative material. The bacteria become pathogenic (negative) and attack the teeth.

The mouthwash or liquid composition of this invention apparently renders various microorganisms, e.g., Streptococci, non-pathogenic by an electrolytic type of action. The microorganisms are prevented from becoming polarized in massive groupings—the liquid composition causes a dispersion of the microorganisms in the body fluids, which keeps them from becoming pathogenic. The mechanism may be that the liquid composition prevents or inhibits the microorganisms from producing toxins. The microorganisms are prevented from becoming morbidly pathogenic.

(The plaque forming bacteria in the mouth stick to the ridges of the teeth. It may be that the mouthwash of this invention achieves plaque formation prevention by not allowing such bacteria from seating and becoming pathogenic. The mouthwash does not open up the enamel to attach by stripping of any protective, non-plaque, non-calculus material from the face of the teeth.)

The mouthwash or liquid composition of this invention is not systemic acting. The mouthwash of this invention is not bacteriostatic or bacteracidal or antibacterial or the like, in the normal sense of such terms. The mouthwash or liquid composition apparently keeps the microorganisms (or brings about a reduction in the microorganisms population).

The composition of this invention can be used as a deodorant. It can be directly applied as a liquid, or can be placed on an absorbent pad or the like and applied in liquid form by putting on the affected surface.

Due to the effect that the mouthwash of this invention has on microorganisms, the mouthwash can be used to eliminate "bad breath", while removing and preventing bad breath. Another application involves the use in the grooming of dogs, cats, etc—for example, the unsightly plaque wand tartar of show animals could be removed, as well as halitosis eliminated, by the mouthwash of this invention.

An important advantage of this invention is that no abrasive material, like that used in most toothpastes and dentifices, has to be used in order to remove and prevent dental plaque formation. A further advantage of this invention is that the mouthwash of this invention eliminates the need to have dentists remove dental plaque from teeth by scrapping with sharpened tools or instruments.

The mouthwash is particularily effective in preventing cavities or caries around metal teeth braces. (Any mouthwash containing HCl or other acid would react with metal teeth braces.)

Unless otherwise stated or indicated, in the following examples and throughout this specification, all percentages, parts and proportions are expressed on a weight basis.

The following examples further illustrate, but do not limit this invention.

EXAMPLE 1

A mouthwash was prepared which contained 5 gm. of sodium oleate, 5 ml. of ethanol, 0.1 gm. of menthol, 0.25 ml. of peppermint flavorant, 0.05 ml of clove flavorant, 10 ml. of sorbitol, 0.1 gm. of sodium benzoate, 0.001 ml. of FD & C blue colorant, and the remainder distilled water (i.e., purified water, USP). The pH of the mouthwash waa adjusted from 9.5 to 9.8 by the addition of 10 cc of NaOH. 0.3 percent by weight of disodium phosphate was added—the pH was 9.92. After two days the pH was 9.9.

EXAMPLE 2

A mouthwash was prepared which contained 5 gm. of sodium oleate, 5 ml. of ethanol, 0.2 gm. of menthol, 0.3 ml. of peppermint flavorant, 0.2 ml. of methylsalicylate, 0.1 ml. of clove flavorant, 10 ml of sorbitol, 0.1 gm. of sodium benzoate, 0.001 ml. of FD & C blue colorant, and the remainder distilled water. The pH of the mouthwash was adjusted from 9.5 to 9.8 by the addition of 10 cc of NaOH. 0.3 percent by weight of disodium phosphate was added—the pH was 9.5. After two days the pH was 9.48.

EXAMPLE 3

A mouthwash was prepared which contained 5 gm. of sodium oleate, 5 ml. of ethanol, 0.1 gm. of menthol, 0.15 ml. of peppermint flavorant, 0.1 ml. of methyl salicylate, 0.05 ml. of clove flavorant, 10 ml of sorbitol, 0.1 gm. of sodium benzoate, 0.001 ml. of FD & C blue colorant, and the remainder distilled water. The pH of the mouthwash was adjusted from 9.5 to 9.8 by the addition of 10 cc of NaOH. 0.3 percent by weight of disodium phosphate was added—the pH was 9.7. After two days the pH was 9.6.

EXAMPLE 4

Example 1 was repeated. The pH went from 9.8 to 9.78 in three days.

EXAMPLE 5

A mouthwash was prepared which contained 5 gm. of sodium oleate, 5 ml. of ethanol, 0.1 gm. of menthol, 0.25 ml of peppermint flavorant, 0.05 ml. of clove flavorant, 10 ml of sorbitol, 0.1 gm. of sodium benzoate and 0.001 ml of FD & C blue colorant and the remainder distilled water. The pH of the mouthwash was adjusted from 9.72 to 9.82 by the addition of 3 cc of NaOH. After two days the pH was 9.8.

EXAMPLE 6

Example 5 was repeated. The pH went from 9.9 to 9.87 in three days.

EXAMPLE 7

A mouthwash was prepared which contained 5 gm. of sodium oleate, 5 ml. of ethanol, 0.2 gm. of menthol, 0.15 ml. of peppermint flavorant, 0.1 ml. of spearmint flavorant, 0.1 ml. of clove flavorant, 10 ml. of sorbitol, 0.1 gm. of sodium benzoate, 0.001 ml. of FD & C blue colorant, 0.3 gm. disodium phosphate and the remainder distilled water. The pH of the mouthwash was adjusted from 9.53 to 9.8 by the addition of 12.5 of NaOH. After two days the pH was 9.8.

EXAMPLE 8

A mouthwash was prepared which contained 5 gm. of sodium oleate, 5 ml. of ethnaol, 0.2 gm. of menthol, 0.3 ml. of peppermint flavorant, 0.1 ml. of clove flavorant, 10 ml. of sorbitol, 0.1 gm. of sodium benzoate, 0.001 gm. of FD & C blue colorant, 0.3 gm. of disodium phosphate and the remainder distilled water. The pH of the mouthwash was adjusted from 9.67 to 9.8 by the addition of 13 cc of NaOH.

EXAMPLE 9

A mouthwash was prepared which contained 5 gm. of sodium oleate, 5 ml. of ethanol, 0.2 gm. of menthol, 0.3 ml. of peppermint flavorant, 0.2 ml. of spearmint flavorant, 0.1 ml. of clove flavorant, 10 ml. of sorbitol, 0.1 gm. of sodium benzoate, 0.001 gm. of FD & C blue colorant, 0.3 gm of disodium phosphate and the remainder distilled water. The pH of the mouthwash was adjusted from 9.5 to 9.8 by the addition of 25 cc of NaOH. (The NaOH used in Examples 1 to 9 was 0.1 N; and the mouthwash volume was 100 ml. in Examples 1 to 9). After two days the pH was 10.1.

EXAMPLE 10

100 ml. of an aqueous solution containing 5 gm. of sodium oleate and 5 ml. of ethanol had a pH of 9.95—after two weeks the pH was 9.72. 100 ml. of an aqueous solution containing 5 gm. of sodium oleate and 10 ml. of ethanol had a pH of 9.84—after two weeks the pH was 9.34. 100 ml. of an aqueous solution containing 5 gm. of sodium oleate and 15 ml. of ethanol had a pH of 9.64—after two weeks the pH was 9.20. 100 ml. of an aqueous solution containing 5 gm. of sodium oleate and 30 ml. of ethanol had a pH of 9.31—after two weeks the pH was 8.93.

EXAMPLE 11

A mouthwash (100 ml) was prepared which contained 5 gm. of sodium oleate, 15 ml. of ethanol, U.S.P. (190°), 0.02 gm. of menthol, U.S.P., 0.2 ml. of oil of peppermint (terpeneless), 0.1 ml of oil of spearmint (terpeneless), 0.1 ml of oil of clove, U.S.P., 10 ml. of sorbitol solution, U.S.P., 0.1 gm. of sodium benzoate, U.S.P., and the remainder purified water, U.S.P. The menthol, peppermint, spearmint, clove and sodium oleate were added to the ethanol. The sorbitol solution and a portion of the water were added. The sodium benzoate and then the rest of the water was added. The mouthwash had a pH of 9.3. The taste was initially flat, but there was a good after taste. The pH of the mouthwash seriously dropped in a few days.

EXAMPLE 12

A mouthwash (100 ml.) was prepared which contained 5 gm. of sodium oleate, 15 ml of ethanol, U.S.P. (190°), 0.02 gm. of menthol, U.S.P., 0.6 ml. of oil of peppermint (terpeneless), 0.1 ml. of oil of spearmint (terpeneless), 0.15 ml of oil of clove, U.S.P., 10 ml. of sorbitol solution, U.S.P., 0.1 gm. of sodium benzoate, U.S.P., 0.1 gm of FD & C Blue No. 1, and the remainder purified water, U.S.P. The mouthwash had a pH of 9.4. The peppermint level was too high, however there was no after taste. The pH of the mouthwash seriously dropped in a few days.

EXAMPLE 13

A mouthwash (100 ml.) was prepared which contained 5 gm. of sodium oleate, 15 ml of ethanol, U.S.P. (190°), 0.4 ml. of oil of peppermint (terpeneless), 0.2 ml. of oil of spearmint (terpeneless), 0.15 ml. of oil of clove, U.S.P., 10 ml. of sorbitol solution, U.S.P., 0.1 gm. of sodium benzoate, U.S.P., a colorant amount of FD & C Blue No. 1, and the remainder purified water, U.S.P. The mouthwash had a pH of 9.4. The taste was good, but there was possibly too much initial bite. The pH of the mouthwash seriously dropped in a few days.

EXAMPLE 14

A mouthwash (100 ml) was prepared which contained 5 gm. of sodium oleate, 15 ml of ethanol, U.S.P. (190°), 0.2 gm. of menthol, U.S.P., 0.1 ml. of methylsalicylate, 0.2 ml. of oil of peppermint (terpeneless), 0.1 ml of oil of clove, U.S.P., 10 ml. of sorbitol, U.S.P., a colorant amount of FD & C Blue No. 1, and the remainder purified water, U.S.P. The mouthwash had a pH of 9.3. The taste was somewhat flat, but the aftertaste was good. The pH of the mouthwash seriously dropped in a few days.

EXAMPLE 15

A mouthwash (100 ml.) was prepared which contained 5 gm. of sodium oleate, 15 ml of ethanol, U.S.P. (190°) 0.2 gm. of menthol, U.S.P., 0.3 ml. of oil of peppermint (terpeneless), 0.2 ml of methyl salicylate, 0.1 ml of oil of clove, U.S.P., 10 ml. of sorbitol solution, U.S.P., 0.1 gm. of sodium benzoate, U.S.P., a colorant amount of FD & C No. 1, and the remainder purified water, U.S.P. The mouthwash had a pH of 9.3. Taste was good. The pH of the mouthwash seriously dropped in a few days.

EXAMPLE 16

A mouthwash (1000 ml.) was prepared which contained 50 gm. of sodium oleate, 150 ml of ethanol, U.S.P. (190°), 2 gm. of menthol, U.S.P., 3 ml. of oil of peppermint (terpeneless), 1 ml. of oil of spearmint (terpeneless), 2 gm. of methyl salicylate, 0.1 ml of oil of clove, U.S.P., 100 ml. of sorbitol solution, U.S.P., 0.1 gm. of sodium benzoate, U.S.P., 0.01 gm of FD & C Blue No. 1, 25 ml. of NaOH (0.1 N) and the remainder purified water, U.S.P. The flavors were dissolved in the ethanol. The sodium oleate was added. The sorbitol solution was added. The colorant and sodium benzoate was dissolved in part of the water—the material was added to the ethanol. The sodium hydroxide was added and then the remainder of the water was added. The pH was about 9.8. The pH of the mouthwash seriously dropped in a few days.

EXAMPLE 17

A person, known to have substantial dental plaque deposits, gargled with about 20 ml. of the mouthwash of Example 9. The gargling was repeated twice a day for three months. Whiteness measurements were made at the start and end of the month period. The person's teeth were substantially whiter, and no new cavities were formed.

EXAMPLE 18

A person having gingivitis, serious receeding of the gums, additional loosened teeth and heavy plaque deposits, gargled twice a day with the mouthwash of Example 9. At the end of the six month period the gingivitis problem was eliminated and the gums had firmed up to such an extent that the teeth were no longer loose and had returned to their original alignment. No new caries was noticed. The general state of the mouth of the person was very much healthier.

EXAMPLE 19

A person having sensitivity syndrome of the teeth gargled with the mouthwash of Example 9.

EXAMPLE 20

Example 9 was repeated using 7.5 ml. of ethanol.

What is claimed is:

1. The mouthwash composition which is a liquefied composition comprised of an effective amount of a non-necrotic fatty acid compound prepared from an unsubstituted, unsaturated fatty acid having at least one double bond, water, an effective amount of a buffering agent, 1 to 10 percent of ethanol, and an effective amount of at least one oil-soluble flavorant the pH of said liquefied composition being between 9 and 11.

2. The mouthwash composition as described in claim 1 wherein said fatty acid compound is a fatty acid salt prepared from an unsaturated fatty acid having one double bond and from an alkali metal or a basic alkali metal or an alkali metal compound or a basic alkali metal compound.

3. The mouthwash composition as claimed in claim 2 wherein said fatty acid compound is sodium oleate.

4. The mouthwash composition as claimed in claim 2 wherein the oil-soluble flavorants are oil of clove, oil of peppermint and oil of spearmint.

5. The mouthwash composition as claimed in claim 2 wherein said buffering agent is disodium phosphate.

6. The mouthwash composition as claimed in claim 2 which contains 2 to 7.5 percent of ethanol.

7. The mouthwash composition as claimed in claim 2 which has a pH between 9.6 and 10.

8. The mouthwash composition as claimed in claim 2 which contains 1 to 10 percent of the fatty acid compound.

9. The mouthwash composition as claimed in claim 2 wherein a thickener is present.

* * * * *